(12) United States Patent
Liu et al.

(10) Patent No.: US 7,943,242 B2
(45) Date of Patent: May 17, 2011

(54) SEALING MEMBERS, ARTICLES USING THE SAME AND METHODS OF REDUCING STICKTION

(75) Inventors: Yongming Liu, Basking Ridge, NJ (US); Xia Zhao, Malvern, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 897 days.

(21) Appl. No.: 11/693,293

(22) Filed: Mar. 29, 2007

(65) Prior Publication Data

US 2007/0228669 A1 Oct. 4, 2007

Related U.S. Application Data

(60) Provisional application No. 60/787,327, filed on Mar. 30, 2006.

(51) Int. Cl.
B32B 13/12 (2006.01)
(52) U.S. Cl. ............................ 428/451; 528/42; 525/478
(58) Field of Classification Search ................... 428/451; 528/42; 525/478
See application file for complete search history.

(56) References Cited

U.S. PATENT DOCUMENTS

| | | | |
|---|---|---|---|
| 4,181,223 A | 1/1980 | Millet | |
| 4,496,695 A | 1/1985 | Sugio et al. | |
| 4,500,310 A | 2/1985 | Christinger | |
| 4,720,521 A | 1/1988 | Spielvogel et al. | |
| 4,764,576 A | 8/1988 | Ogawa et al. | |
| 4,767,414 A | 8/1988 | Williams et al. | |
| 4,806,430 A | 2/1989 | Spielvogel et al. | |
| 4,822,632 A | 4/1989 | Williams et al. | |
| 4,842,889 A | 6/1989 | Hu et al. | |
| 4,844,986 A | 7/1989 | Karakelle et al. | |
| 4,959,402 A | 9/1990 | Williams et al. | |
| 4,994,552 A | 2/1991 | Williams et al. | |
| 4,997,423 A | 3/1991 | Okuda et al. | |
| 5,186,972 A | 2/1993 | Williams et al. | |
| 5,266,359 A | 11/1993 | Spielvogel | |
| 5,288,560 A | 2/1994 | Sudo et al. | |
| 5,338,312 A | 8/1994 | Montgomery | |
| 5,578,340 A | 11/1996 | Ogawa et al. | |
| 5,587,244 A | 12/1996 | Flinchbaugh | |
| 5,607,400 A | 3/1997 | Thibault et al. | |
| 5,736,251 A | 4/1998 | Pinchuk | |
| 5,849,369 A | 12/1998 | Ogawa | |
| 5,853,894 A | 12/1998 | Brown | |
| 6,046,143 A | 4/2000 | Khan et al. | |
| 6,065,270 A | 5/2000 | Reinhard et al. | |
| 6,200,627 B1 * | 3/2001 | Lubrecht | 427/2.28 |
| 6,243,938 B1 | 6/2001 | Lubrecht | |
| 6,296,893 B2 | 10/2001 | Heinz et al. | |
| 6,447,835 B1 | 9/2002 | Wang et al. | |
| 6,458,867 B1 | 10/2002 | Wang et al. | |
| 6,562,010 B1 | 5/2003 | Gyure et al. | |
| 6,586,039 B2 | 7/2003 | Heinz et al. | |
| 6,746,430 B2 | 6/2004 | Lubrecht | |
| 7,041,088 B2 | 5/2006 | Nawrocki et al. | |
| 2001/0004466 A1 | 6/2001 | Heinz | |
| 2003/0100696 A1 | 5/2003 | Muraki | |
| 2004/0082917 A1 | 4/2004 | Hetzler | |
| 2004/0209784 A1 | 10/2004 | Hardman et al. | |
| 2007/0148326 A1 | 6/2007 | Hastings et al. | |
| 2007/0228669 A1 | 10/2007 | Liu | |
| 2007/0287954 A1 | 12/2007 | Zhao | |
| 2008/0069970 A1 | 3/2008 | Wu | |

FOREIGN PATENT DOCUMENTS

| | | |
|---|---|---|
| EP | 0164583 A2 | 12/1985 |
| EP | 1 064 037 B1 | 1/2001 |
| EP | 1227126 A1 | 7/2002 |
| JP | 57 182418 | * 11/1982 |
| JP | 05-339505 | * 12/1993 |
| JP | 2005097401 | 4/2005 |
| WO | 99 44754 A1 | 9/1999 |
| WO | 99 44755 A1 | 9/1999 |
| WO | 9947192 A | 9/1999 |
| WO | 2004009146 A1 | 1/2004 |
| WO | 2004064901 A2 | 8/2004 |
| WO | 2004083348 A2 | 9/2004 |

OTHER PUBLICATIONS

Silicones—G.G. Freeman, published for the Plastics Institute, ILIFE Bonks Ltd. (1962) (pp. 79-80).*
Material Safety Data Sheet for LSR Topcoat Part A, GE Silicones, Jan. 20, 2004.
Material Safety Data Sheet for LSR Topcoat Part B, GE Silicones, Jan. 22, 2004.

* cited by examiner

*Primary Examiner* — Kuo-Liang Peng
(74) *Attorney, Agent, or Firm* — David M. Fortunato; The Webb Law Firm (57) ABSTRACT

The present invention provides rubber sealing members having an exterior surface adapted to sealingly engage an inner surface of a chamber of the medical device, the exterior surface of the sealing member having a coating thereon prepared from a curable composition including: (a) a first organopolysiloxane having at least two alkenyl groups; and (b) a second organopolysiloxane having at least two pendant hydrogen groups, the second organopolysiloxane being different from the first organopolysiloxane, wherein at least one of the first organopolysiloxane, the second organopolysiloxane or an optional third organopolysiloxane of the curable composition comprises a fluoro group.

39 Claims, 7 Drawing Sheets

SEALING MEMBERS, ARTICLES USING THE SAME AND METHODS OF REDUCING STICKTION

CROSS REFERENCE TO RELATED APPLICATIONS

The present application claims priority to provisional application No. 60/787,327 filed on Mar. 30, 2006.

BACKGROUND OF THE INVENTION

1. Field of the Invention

This invention relates to a rubber sealing member for a medical device, such as a syringe assembly, coated with a composition comprising curable organopolysiloxane(s), methods to reduce static and kinetic friction between slidable surfaces; and articles of low friction prepared thereby.

2. Description of Related Art

Certain devices require slow and controlled initiation and maintenance of sliding movement of one surface over another surface. It is well known that two stationary surfaces having a sliding relationship often exhibit sufficient resistance to initiation of movement that gradually increased pressure applied to one of the surfaces does not cause movement until a threshold pressure is reached, at which point a sudden sliding separation of the surfaces takes place. This sudden separation of stationary surfaces into a sliding relationship is herein referred to as "breakout".

A less well known, but important frictional force is "breakloose force", which refers to the force required to overcome static friction between surfaces of a syringe assembly that has been subjected to autoclaving and may have a slight deformation in one or both of the contacting surfaces of the syringe assembly, for example in the syringe barrel. In addition to autoclaving, parking of the assembly can further increase the breakloose force.

Breakout and breakloose forces are particularly troublesome in liquid dispensing devices, such as syringes, used to deliver small, accurately measured quantities of a liquid by smooth incremental line to line advancement of one surface over a graduated second surface. The problem is also encountered in devices using stopcocks, such as burets, pipets, addition funnels and the like where careful dropwise control of flow is desired.

The problems of excessive breakout and breakloose forces are related to friction. Friction is generally defined as the resisting force that arises when a surface of one substance slides, or tends to slide, over an adjoining surface of itself or another substance. Between surfaces of solids in contact, there may be two kinds of friction: (1) the resistance opposing the force required to start to move one surface over another, conventionally known as static friction, and (2) the resistance opposing the force required to move one surface over another at a variable, fixed, or predetermined speed, conventionally known as kinetic friction.

The force required to overcome static friction and induce breakout is referred to as the "breakout force", and the force required to maintain steady slide of one surface over another after breakout or breakloose is referred to as the "sustaining force". Two main factors contribute to static friction and thus to the breakout or breakloose force. The term "stick" as used herein denotes the tendency of two surfaces in stationary contact to develop a degree of adherence to each other. The term "inertia" is conventionally defined as the indisposition to motion which must be overcome to set a mass in motion. In the context of the present invention, inertia is understood to denote that component of the breakout force which does not involve adherence.

Breakout or breakloose forces, in particular the degree of stick, vary according to the composition of the surfaces. In general, materials having elasticity show greater stick than non-elastic materials, particularly when the surfaces are of dissimilar composition. The length of time that surfaces have been in stationary contact with each other also influences breakout and/or breakloose forces. In the syringe art, the term "parking" denotes storage time, shelf time, or the interval between filling and discharge. Parking generally increases breakout or breakloose force, particularly if the syringe has been refrigerated during parking.

A conventional approach to overcoming breakout has been application of a lubricant to a surface to surface interface. Common lubricants used are hydrocarbon oils, such as mineral oils, peanut oil, vegetable oils and the like. Such products have the disadvantage of being soluble in a variety of fluids, such as vehicles commonly used to dispense medicaments. In addition, these lubricants are subject to air oxidation resulting in viscosity changes and objectionable color development. Further, they are particularly likely to migrate from the surface to surface interface. Such lubricant migration is generally thought to be responsible for the increase in breakout force with time in parking.

Silicone oils are also commonly used as lubricants. They are poor solvents and are not subject to oxidation, but migration and stick do occur, and high breakout forces are a problem. Polytetrafluoroethylene surfaces provide some reduction in breakout forces, but this material is very expensive, and the approach has not been totally effective.

Thus there is a need for a better system to overcome high breakout and breakloose forces whereby smooth transition of two surfaces from stationary contact into sliding contact can be achieved.

SUMMARY OF THE INVENTION

In some embodiments, the present invention provides a rubber sealing member for a medical device, the sealing member having an exterior surface adapted to sealingly engage an inner surface of a chamber of the medical device, the exterior surface of the sealing member having a coating thereon prepared from a curable composition comprising:

(a) a first organopolysiloxane comprising at least two alkenyl groups; and (b) a second organopolysiloxane comprising at least two pendant hydrogen groups, the second organopolysiloxane being different from the first organopolysiloxane, wherein at least one of the first organopolysiloxane, the second organopolysiloxane or an optional third component of the curable composition comprises at least one fluoro group.

In some embodiments, the present invention provides articles of manufacture, such as medical devices, comprising the rubber sealing member of the present invention.

In some embodiments, the present invention provides a method for lubricating the interface between an inner surface of a chamber and an exterior surface of a rubber sealing member of a medical device, comprising the steps of:

(a) applying a coating onto the exterior surface of the rubber sealing member, the coating being prepared from a curable composition comprising:

(i) a first organopolysiloxane comprising at least two alkenyl groups; and (ii) a second organopolysiloxane comprising at least two pendant hydrogen groups, the second organopolysiloxane being different from the first organopolysiloxane, wherein at least one of the first organopolysiloxane, the second organopolysiloxane or an optional third component of the curable composition comprises at least one fluoro group; and (b) at least partially crosslinking the coating of step (a).

In other embodiments, the present invention provides a method for reducing breakout force or breakloose force between an inner surface of a chamber and an exterior surface of a rubber sealing member of a medical device, comprising the steps of:

(a) applying a coating onto the exterior surface of the rubber sealing member, the coating being prepared from a curable composition comprising:

(i) a first organopolysiloxane comprising at least two alkenyl groups; and (ii) a second organopolysiloxane comprising at least two pendant hydrogen groups, the second organopolysiloxane being different from the first organopolysiloxane, wherein at least one of the first organopolysiloxane, the second organopolysiloxane or an optional third component of the curable composition comprises at least one fluoro group; and (b) at least partially crosslinking the coating of step (a).

In other embodiments, the present invention provides a method for reducing sustaining force between an inner surface of a chamber and an exterior surface of a rubber sealing member of a medical device, comprising the steps of:

(a) applying a coating onto the exterior surface of the rubber sealing member, the coating being prepared from a curable composition comprising:

(i) a first organopolysiloxane comprising at least two alkenyl groups; and (ii) a second organopolysiloxane comprising at least two pendant hydrogen groups, the second organopolysiloxane being different from the first organopolysiloxane, wherein at least one of the first organopolysiloxane, the second organopolysiloxane or an optional third component of the curable composition comprises at least one fluoro group; and (b) at least partially crosslinking the coating of step (a).

In other embodiments, the present invention provides a method for reducing breakloose and sustaining forces between an inner surface of a chamber and an exterior surface of a rubber sealing member of a medical device, comprising the steps of:

(a) applying a coating onto the exterior surface of the rubber sealing member, the coating being prepared from a curable composition comprising:

(i) a first organopolysiloxane comprising at least two alkenyl groups; and (ii) a second organopolysiloxane comprising at least two pendant hydrogen groups, the second organopolysiloxane being different from the first organopolysiloxane, wherein at least one of the first organopolysiloxane, the second organopolysiloxane or an optional third component of the curable composition comprises at least one fluoro group; and (b) at least partially crosslinking the coating of step (a).

BRIEF DESCRIPTION OF THE DRAWINGS

The present invention will best be understood from the following description of specific embodiments when read in connection with the accompanying drawings.

DETAILED DESCRIPTION OF THE INVENTION

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

The present invention provides a rubber sealing member having an exterior surface adapted to sealingly engage an inner surface of a chamber of a medical device. The respective surfaces can be in frictional engagement. When used in a medical device, the rubber sealing member of the present invention can reduce the force required to achieve breakout, breakloose and/or sustaining forces, whereby transition of surfaces from stationary contact to sliding contact occurs without a sudden surge. When breakout or breakloose is complete and the surfaces are in sliding contact, they slide smoothly upon application of very low sustaining force. Substantially less lubricant may be required and lubricant migration is reduced or eliminated. The effect achieved by the sealing member and methods of the present invention can be of long duration, and articles, such as syringes, can retain the advantages of low breakout, low breakloose and sustaining forces throughout any parking period. When the sealing member is part of a liquid dispensing device, small highly accurate increments of liquid may be dispensed repeatedly without sudden surges. Thus, a syringe including a rubber sealing member treated according to the present invention can be used to administer a medicament to a patient without the danger of surges whereby accurate control of dosage and greatly enhanced patient safety are realized.

Non-limiting examples of medical devices include syringe assemblies, syringe pumps, drug cartridges, needleless injectors, liquid dispensing devices and liquid metering devices. In some embodiments, the medical device is a syringe assembly comprising a first component which is a sealing member and a second component which is a syringe barrel.

The rubber sealing member can be formed from any elastomeric material. Elastomers are used in many important and critical applications in medical devices and pharmaceutical packaging. As a class of materials, their unique characteristics, such as flexibility, resilience, extendability, and sealability, have proven particularly well suited for products such as catheters, syringe tips, drug vial articles, injection sites, tubing, gloves and hoses. Three primary synthetic thermoset elastomers typically are used in medical applications: polyisoprene rubber, silicone rubber, and butyl rubber. Of the three rubbers, butyl rubber has been the most common choice for articles due to its high cleanness and permeation resistance which enables the rubber to protect oxygen- and water-sensitive drugs.

Suitable butyl rubbers useful in the method of the present invention include copolymers of isobutylene (about 97-98%) and isoprene (about 2-3%). The butyl rubber can be halogenated with chlorine or bromine. Suitable butyl rubber vulcanizates can provide good abrasion resistance, excellent impermeability to gases, a high dielectric constant, excellent resistance to aging and sunlight, and superior shock-absorbing and vibration-damping qualities to articles formed therefrom.

Other useful elastomeric copolymers include, without limitation, styrene copolymers such as styrene-butadiene (SBR or SBS) copolymers, styrene-isoprene (SIS) block polymers or styrene-isoprene/butadiene (SIBS), in which the content of styrene in the styrene block copolymer ranges from about 10% to about 70%, and preferably from about 20% to about 50%. The rubber composition can include, without limitation, antioxidants and/or inorganic reinforcing agents to preserve the stability of the rubber composition.

In some embodiments, the sealing member can be a stopper, O-ring, plunger tip or piston, for example. Syringe plunger tips or pistons typically are made of a compressible, resilient material such as butyl rubber, because of the vulcanized rubber's ability to provide a seal between the plunger and interior housing of the syringe. Syringe plungers, like other equipment used in the care and treatment of patients, have to meet high performance standards, such as the ability to provide a tight seal between the plunger and the barrel of the syringe.

The coating is applied to at least a portion of at least one surface of the rubber sealing member to be placed in frictional engagement with an opposed surface of another component. The other component of the medical device, such as the barrel, can be coated with a coating as described below for the sealing member, a polydimethylsiloxane coating or uncoated, as desired. Methods for coating the surface(s) are discussed in detail below.

The rubber sealing member of the present invention is coated with a cured coating prepared from a composition comprising a first organopolysiloxane comprising at least two alkenyl groups; and (b) a second organopolysiloxane comprising at least two pendant hydrogen groups, the second organopolysiloxane being different from the first organopolysiloxane, wherein at least one of the first organopolysiloxane, the second organopolysiloxane or an optional third component of the curable composition comprises at least one fluoro group, as described in detail below. As used herein, the term "cure" as used in connection with a composition, e.g., a "cured composition" or a "cured coating" shall mean that at least a portion of the crosslinkable components which form the composition are at least partially crosslinked. As used herein, the term "curable", as used in connection with a component of the composition, means that the component has functional groups capable of being crosslinked, for example alkenyl groups such as vinyl groups. In certain embodiments of the present invention, the crosslink density of the crosslinkable components, i.e., the degree of crosslinking, ranges from 5% to 100% of complete crosslinking. One skilled in the art will understand that the presence and degree of crosslinking, i.e., the crosslink density, can be determined by a variety of methods, such as dynamic mechanical thermal analysis (DMTA) using a TA Instruments DMA 2980 DMTA analyzer conducted under nitrogen. This method determines the glass transition temperature and crosslink density of free films of coatings or polymers. These physical properties of a cured material are related to the structure of the crosslinked network.

As discussed above, the coating composition comprises one or more first, curable organopolysiloxane(s) comprising at least two alkenyl groups. Each alkenyl group of the first organopolysiloxane (a) can be independently selected from the group consisting of vinyl, allyl, propenyl, butenyl, pentenyl, hexenyl, heptenyl, octenyl, nonenyl and decenyl. One skilled in the art would understand that the first organopolysiloxane (a) can comprise one or more of any of the above types of alkenyl groups and mixtures thereof. In some embodiments, at least one alkenyl group is vinyl. Higher alkenyl or vinyl content provides more efficient crosslinking.

In some embodiments, the first organopolysiloxane (a) can be represented by the following structural formulae (I) or (II):

wherein R is alkyl, haloalkyl, aryl, haloaryl, cycloalkyl, silacyclopentyl, aralkyl and mixtures thereof; X is about 60 to about 1000, preferably about 200 to about 320; and y is about 3 to about 25. Copolymers and mixtures of these polymers are also contemplated.

Non-limiting examples of useful first organopolysiloxanes (a) include: vinyldimethyl terminated polydimethylsiloxanes; vinylmethyl, dimethylpolysiloxane copolymers; vinyldimethyl terminated vinylmethyl, dimethylpolysiloxane copolymers; divinylmethyl terminated polydimethylsiloxanes; polydimethylsiloxane, mono vinyl, mono n-butyldimethyl terminated; and vinylphenylmethyl terminated polydimethylsiloxanes.

In some embodiments, a mixture of siloxane polymers selected from those of Formulae I and/or II can be used. For example, the mixture can comprise two different molecular weight vinyldimethylsilyl terminated polydimethylsiloxane polymers, wherein one of the polymers has an average molecular weight of about 5,000 to about 25,000 and preferably about 16,000, and the other polymer has an average molecular weight of about 30,000 to about 75,000 and preferably about 38,000. Generally, the lower molecular weight siloxane can be present in amounts of about 20% to about 80%, such as about 60% by weight of this mixture; and the higher molecular weight siloxane can be present in amounts of about 80% to about 20%, such as about 40% by weight of this mixture.

Another non-limiting example of a suitable first organopolysiloxane (a) is (7.0-8.0% vinylmethylsiloxane)-dimethylsiloxane copolymer, trimethylsiloxy terminated, such as VDT-731 vinylmethylsiloxane copolymer which is commercially available from Gelest, Inc. of Morrisville, Pa.

In some embodiments, the first organopolysiloxane (a) can further comprise one or more fluoro groups, such as —F or fluoroalkyl groups such as trifluoromethyl groups.

In some embodiments, the first organopolysiloxane (a) can further comprise one or more alkyl and/or one or more aryl groups, such as methyl groups, ethyl groups or phenyl groups, respectively.

Generally, the viscosity of the alkenyl-substituted siloxanes can range from about 200 to about 1,000,000 cst.

In some embodiments, the first organopolysiloxane (a) comprises about 5 to about 50 weight percent of the composition. In other embodiments, the first organopolysiloxane (a) comprises about 10 to about 40 weight percent of the composition. In other embodiments, the first organopolysiloxane (a) comprises about 15 to about 30 weight percent of the composition.

While not wishing to be bound by any theory, it is believed that the alkenyl functional siloxanes can increase the viscosity of the coating and improve binding between the coating and the coated surface.

The composition also comprises one or more second organopolysiloxane(s) (b) comprising at least two pendant hydrogen groups, the second organopolysiloxane (b) being different from the first organopolysiloxane, for example having different types of atom(s) or different numbers of atoms in the respective organopolysiloxanes.

Non-limiting examples of suitable organopolysiloxanes (b) comprising at least two pendant hydrogen groups include organopolysiloxanes having pendant hydrogen groups along the polymer backbone or terminal hydrogen groups. In some embodiments, the organopolysiloxane can be represented by the following structural formulae (V):

wherein p is about 8 to about 12, for example about 10. In other embodiments, the organopolysiloxane can be represented by the following structural formula (VI):

wherein p is about 140 to about 170, for example about 150 to about 160. A mixture of these polymers can be used comprising two different molecular weight materials. For example, about 2% to about 5% by weight of the mixture of a trimethyl silyl terminated polymethylhydrogensiloxane having an average molecular weight of about 400 to about 7,500, for example about 1900, can be used in admixture with about 98% to about 95% of a dimethylhydrogen silyl-terminated polymethylhydrogensiloxane having an average molecular weight of about 400 to about 37,000 and preferably about 12,000. In some embodiments, the mole ratio of vinyl groups to hydrogen groups in the reactive component is about 0.010:1 to about 0.20:1. In some embodiments, the mole ratio of hydrogen groups of the crosslinking polymer to hydrogen groups of the chain-extending polymer is about 5.0:1 to about 20:1. Non-limiting example of useful organopolysiloxanes comprising at least two pendant hydrogen groups include dimethylhydro terminated polydimethylsiloxanes; methylhydro, dimethylpolysiloxanecopolymers; methylhydro terminated methyloctyl siloxane copolymers; and methylhydro, phenylmethyl siloxane copolymers.

In some embodiments, the second organopolysiloxane (b) can further comprise one or more fluoro groups, such as —F or fluoroalkyl groups such as trifluoromethyl groups.

In some embodiments, the second organopolysiloxane (b) can further comprise one or more alkyl and/or one or more aryl groups, such as methyl groups, ethyl groups or phenyl groups, respectively.

Generally, the viscosity of the hydrogen substituted siloxane can range from about 100 to about 1,000,000 cst.

In some embodiments, the second organopolysiloxane (b) comprises about 1 to about 40 weight percent of the composition. In other embodiments, the second organopolysiloxane (b) comprises about 5 to about 30 weight percent of the composition. In other embodiments, the second organopolysiloxane (b) comprises about 10 to about 30 weight percent of the composition.

In some embodiments, the composition can further comprise one or more third components comprising at least one fluoro group, for example fluorine groups and/or fluoroalkyl groups. Non-limiting examples of such third components comprise one or more fluorocarbon oligomers, fluorocarbon polymers and/or fluoro organopolysiloxanes, such as polytetrafluoroethylene, polymers of chlorotrifluoroethylene, fluorinated ethylene-propylene polymers, polyvinylidene fluoride, hexafluoropropylene, and the like, preferably suitable for medical applications.

When present, the third component can comprise about 0.1 to about 20 weight percent of the composition. In other embodiments, the third component comprises about 0.1 to about 10 weight percent of the composition.

In some embodiments, the composition can further comprise one or more cyclic siloxane(s), for example octamethylcyclotetrasiloxane and/or decamethylcyclopentasiloxane. In some embodiments, the cyclic siloxane comprises about 5 to about 80 weight percent of the composition. In other embodiments, the cyclic siloxane comprises about 20 to about 80 weight percent of the composition. In other embodiments, the cyclic siloxane comprises about 40 to about 80 weight percent of the composition.

In some embodiments, the composition further comprises one or more organopolysiloxane(s) different from the first and second organopolysiloxanes, for example siloxanes of Formula (IV) shown below, such as alkyl siloxanes.

Non-limiting examples of such organopolysiloxanes can be represented by the following structural formula (IV):

wherein R is alkyl, haloalkyl, aryl, haloaryl, cycloalkyl, silacyclopentyl, aralkyl and mixtures thereof; and Z is about 20 to about 1,800. In some embodiments, the organopolysiloxanes of Formula (IV) can be represented by the following structural formula (IVA):

wherein Z can be as above, or for example can be about 70 to about 1800 or about 70 to about 1,350. The average molecular weight of the organopolysiloxane of Formula (IV) can be about 1900 to about 100,000, and preferably about 5,000 to about 100,000. Generally, this corresponds with a viscosity of about 20 to about 300,000 centistokes (cst).

A non-limiting example of a suitable alkyl organosiloxane is polydimethylsiloxane. The viscosity of the alkyl organosiloxane can range from about 100 to about 1,000,000 cst, and in some embodiments can range from about 12,500 to about 100,000 cst. In some embodiments, the alkyl organosiloxane comprises about 1 to about 20 weight percent of the composition. In other embodiments, the alkyl organosiloxane comprises about 1 to about 10 weight percent of the composition. In other embodiments, the alkyl organosiloxane comprises about 1 to about 5 weight percent of the composition.

In some embodiments, the composition further comprises silica, which can adjust the hardness of the coating. In some embodiments, the silica comprises about 1 to about 15 weight percent of the composition. In other embodiments, the silica comprises about 1 to about 10 weight percent of the composition. In other embodiments, the silica comprises about 1 to about 5 weight percent of the composition.

In some embodiments, the composition further comprises a catalytic amount of a catalyst for promoting crosslinking of the first organopolysilaxane (a) and the second organopolysiloxane (b). Non-limiting examples of suitable catalysts for promoting heat cure include platinum or rhodium group metal catalysts, such as Karstedt catalyst $Pt_2\{[(CH_2=CH)Me_2Si]_2O\}_3$ or peroxide catalysts, such as dicumyl peroxide The catalyst can be present in an amount ranging from about 0.001 to about 0.05 weight percent of the composition.

The components of the composition can be formulated in a single composition or two compositions that are mixed prior to application, for example to separate a catalyst from crosslinkable components until shortly before application. A non-limiting example of a suitable composition is a two-part composition commercially available from GE Advanced Materials as LSR Topcoat Parts A and B, which are mixed before application to the rubber sealing member. According to a Material Safety Data Sheet dated Jan. 20, 2004, LSR Topcoat Part A contains greater than about 99% decamethylcyclopentasiloxane and less that about 1% octamethylcyclotetrasiloxane. According to a Material Safety Data Sheet dated Jan. 22, 2004, LSR Topcoat Part B contains greater than about 50% decamethylcyclopentasiloxane, less than about 25% vinyl-terminated polydimethylsiloxane, less than 10% synthetic amorphous silica, precipitated, less than 5% polydimethylsiloxane, and greater than 10% of silanic hydrogen fluid. Part A and Part B can be mixed up to about a day before application to the rubber sealing member, and are preferably mixed shortly before application. Generally, about 50 weight percent of Part A and about 50 weight percent of Part B are used to prepare the composition, although the relative amounts can be varied if desired.

In some embodiments, the composition can further comprise one or more curable organopolysiloxane(s) comprising at least two polar groups, being different from the first organopolysiloxane(s) and second organopolysiloxane(s), for example having different types of atom(s) or different numbers of atoms in the respective organopolysiloxanes.

Each polar group of the organopolysiloxane can be independently selected from the group consisting of acrylate, methacrylate, amino, imino, hydroxy, epoxy, ester, alkyloxy, isocyanate, phenolic, polyurethane oligomeric, polyamide oligomeric, polyester oligomeric, polyether oligomeric, polyol, carboxypropyl, and fluoro groups. One skilled in the art would understand that the organopolysiloxane can comprise one or more of any of the above polar groups and mixtures thereof. Preferably, these organopolysiloxanes are not moisture-curable.

In some embodiments, the polar groups are acrylate groups, for example acryloxypropyl groups. In other embodiments, the polar groups are methacrylate groups, such as methacryloxypropyl groups.

The organopolysiloxane having polar groups can further comprise one or more alkyl groups and/or aryl groups, such as methyl groups, ethyl groups or phenyl groups.

A non-limiting example of such an organopolysiloxane is [15-20% (acryloxypropyl)methylsiloxane]-dimethylsiloxane copolymer, such as UMS-182 acrylate functional siloxane which is commercially available from Gelest, Inc. of Morrisville, Pa. Other useful organopolysiloxanes (b) include polyfluoroalkylmethyl siloxanes and fluoroalkyl, dimethyl siloxane copolymers.

In other embodiments, such an organopolysiloxane can be represented by the formula (III):

wherein $R_1$ is selected from the group consisting of acrylate, methacrylate, amino, imino, hydroxy, epoxy, ester, alkyloxy, isocyanate, phenolic, polyurethane oligomeric, polyamide oligomeric, polyester oligomeric, polyether oligomeric, polyol, carboxypropyl, and fluoro groups, and $R_2$ is alkyl, n ranges from 2 to 4, and x is an integer sufficient to give the lubricant a viscosity of about 10 to 2,000,000 cst.

In some embodiments, the organopolysiloxane having polar groups comprises about 1 to about 40 weight percent of the composition, in other embodiments about 3 to about 20 weight percent, and in other embodiments, about 1 to about 20 weight percent of the composition.

While not wishing to be bound by any theory, it is believed that the polar siloxanes may be present on top of the coated surface to help reduce the coefficient of friction between the engaged surfaces. Also, after irradiation, it is believed that the viscosity of the polar siloxane may increase and improve the binding of the coating to substrate.

In some embodiments, the composition is essentially free of moisture-curable siloxanes, for example a moisture-curable siloxane comprising at least two hydroxyl groups, such as for example:

(VII)

wherein $R_2$ is alkyl, n ranges from 2 to 4, and x is an integer sufficient to give the lubricant a viscosity of about 10 to 2,000,000 cst. Other moisture-curable siloxanes which have moisture-curing character as a result of functionality include siloxanes having functional groups such as: alkoxy, aryloxy; oxime; epoxy; —OOCR$_{13}$, N,N-dialkylamino; N,N-dialkylaminoxy; N-alkylamido; —O—NH—C(O)—R$_{13}$ ; —O—C(=NCH$_3$)—NH—CH$_3$, —O—C(CH$_3$)=CH$_2$ ; and —S—C$_3$H$_6$Si(OCH$_3$)$_3$ ; wherein R$_{13}$ is H or hydrocarbyl. As used herein, "moisture-curable" means that the siloxane is curable at ambient conditions in the presence of atmospheric moisture. As used herein, "essentially free of moisture-curable siloxanes" means that the composition includes less than about 5 weight percent of moisture-curable siloxanes, in some embodiments less than about 2 weight percent, and in other embodiments is free of moisture-curable siloxanes.

The other component of the medical device in contact with the sealing member can be formed from glass, metal, ceramic, plastic, rubber or combinations thereof. In some embodiments, the component is prepared from one or more olefinic polymers, such as polyethylene, polypropylene, poly(1-butene), poly(2-methyl-1-pentene) and/or cyclic polyolefin. For example, the polyolefin can be a homopolymer or a copolymer of an aliphatic monoolefin, the aliphatic monoolefin preferably having about 2 to 6 carbon atoms, such as polypropylene. In some embodiments, the polyolefin can be basically linear, but optionally may contain side chains such as are found, for instance, in conventional, low density polyethylene. In some embodiments, the polyolefin is at least 50% isotactic. In other embodiments, the polyolefin is at least about 90% isotactic in structure. In some embodiments, syndiotactic polymers can be used. A non-limiting example of a suitable cyclic polyolefin includes an ethylene-norbornene copolymer such as TOPAS® ethylene-norbornene copolymer commercially available from Ticona Engineering Polymers of Florence, Ky.

The polyolefin can contain a small amount, generally from about 0.1 to 10 percent, of an additional polymer incorporated into the composition by copolymerization with the appropriate monomer. Such copolymers may be added to the composition to enhance other characteristics of the final composition, and may be, for example, polyacrylate, polyvinyl, polystyrene and the like.

In some embodiments, the other component may be constructed of a polyolefin composition which includes a radiation stabilizing additive to impart radiation stability to the container, such as a mobilizing additive which contributes to the radiation stability of the container, such as for example those disclosed in U.S. Pat. Nos. 4,959,402 and 4,994,552, assigned to Becton, Dickinson and Company and both of which are incorporated herein by reference.

Application of a film of coating to the surface of the sealing member may be accomplished by any suitable method, as, for example, dipping, brushing, spraying and the like. The composition may be applied neat or it may be applied in a solvent, such as low molecular weight silicone, non-toxic chlorinated or fluorinated hydrocarbons, for example, 1,1,2-trichloro-1,2,2-trifluoroethane, freon or conventional hydrocarbon solvents such as alkanes, toluene, petroleum ether and the like where toxicology is not considered important. The solvent is subsequently removed by evaporation. The lubricant film may be of any convenient thickness and, in practice, the thickness will be determined by such factors as the viscosity of the lubricant and the temperature of application. For reasons of economy, the film preferably is applied as thinly as practical, since no significant advantage is gained by thicker films.

The inventive compositions can be fully cured after application or partially cured to attach them to the substrate, and then fully cured at a later time. For example, air drying will permit partial cure. The compositions are initially fluid and can be applied directly to the substrate in any suitable manner, for example by dipping, brushing or spraying. The exact thickness of the coating does not appear to be critical and very thin coatings, e.g., one or two microns exhibit effective lubricating properties. While not necessary for operability, it is desirable that the thickness of the coating be substantially uniform throughout.

Curing of the reactive portion can be accomplished by conventional methods well known in the art. For example, curing by use of a catalyst, heat curing via oven or radio frequency (RF) are useful methods as well as the use of gamma, e-beam or ultraviolet radiation. Any mechanism which will initiate the hydrosilylation reaction is a useful curing technique.

In some embodiments, the coating is at least partially cured by irradiation with an isotope or electron beam. Radiation sterilization in the form of ionizing radiation commonly is used in hospitals for medical devices such as catheters, surgical items and critical care tools. Gamma irradiation is the most popular form of radiation sterilization and typically is used when materials are sensitive to the high temperature of autoclaving but are compatible with ionizing radiation. The bactericidal effect of gamma irradiation exerts its microbicidal effect by oxidizing biological tissue, and thus provides a simple, rapid and efficacious method of sterilization. Gamma rays are used either from a cobalt-60 ($^{60}$Co) isotope source or from a machine-generated accelerated electron source. Sufficient exposures are achieved when the materials to be sterilized are moved around an exposed $^{60}$Co source for a defined period of time. The most commonly used validated dose for sterilizing medical devices is about 10 to about 100 kGy, for example 20-50 kGy.

In the case of oven curing, temperatures should range from about 150° to about 180° C. and residence time in the oven is generally about 30 to about 40 seconds, depending on the precise formulation. If RF techniques are used, the coil should conduct enough heat to obtain a substrate surface temperature of about 180° to about 240° C. At these temperatures, only about 2 to about 4 seconds are required for cure. If gamma radiation techniques are used, the need for hydrosilylation initiating catalyst is eliminated, since the radiation will start the cure. This technique has the advantage of sterilizing as well, which is useful in medical applications.

In some embodiments, the coated articles are subjected to a sterilization treatment. Many sterilization techniques are available today to sterilize medical devices to eliminate living organisms such as bacteria, yeasts, mold and viruses. Commonly used sterilization techniques used for medical devices include autoclaving, ethylene oxide (EtO) or gamma irradiation, as well as more recently introduced systems that involve low-temperature gas plasma and vapor phase sterilants.

One common sterilization technique is steam sterilization or autoclaving, which is a relatively simple process that exposes a device, for example, to saturated steam at temperatures of over 120° C. for a minimum of twenty minutes at a pressure of about 120 kPa. The process is usually carried out in a pressure vessel designed to withstand the elevated temperature and pressure to kill microorganisms by destroying metabolic and structural components essential to their replication. Autoclaving is the method of choice for sterilization of heat-resistant surgical equipment and intravenous fluid as it is an efficient, reliable, rapid, relatively simple process that does not result in toxic residues.

Thus, in some embodiments, the present invention provides a method for lubricating the interface between an inner surface of a chamber and an exterior surface of a rubber sealing member of a medical device, comprising the steps of: (a) applying a coating as described above onto the exterior surface of the rubber sealing member; and (b) at least partially crosslinking the coating of step (a).

In other embodiments, the present invention provides a method for reducing breakout force or breakloose force between an inner surface of a chamber and an exterior surface of a rubber sealing member of a medical device, comprising the steps of: (a) applying a coating as described above onto the exterior surface of the rubber sealing member; and (b) at least partially crosslinking the coating of step (a).

In other embodiments, the present invention provides a method for reducing sustaining force between an inner surface of a chamber and an exterior surface of a rubber sealing member of a medical device, comprising the steps of: (a) applying a coating as described above onto the exterior surface of the rubber sealing member; and (b) at least partially crosslinking the coating of step (a).

In other embodiments, the present invention provides a method for reducing breakloose and sustaining forces between an inner surface of a chamber and an exterior surface of a rubber sealing member of a medical device, comprising the steps of: (a) applying a coating as described above onto the exterior surface of the rubber sealing member; and (b) at least partially crosslinking the coating of step (a).

Breakout forces, breakloose forces and sustaining forces may be conveniently measured on a universal mechanical tester or on a testing machine of the type having a constant rate of cross-head movement, as, for example an Instron model 1122, as described in detail below.

The present invention is more particularly described in the following examples, which are intended to be illustrative only, as numerous modifications and variations therein will be apparent to those skilled in the art.

EXAMPLES

Example 1

In this example, rubber stoppers for a 10 ml syringe were coated with a conventional polydimethylsiloxane or a coating composition according to the present invention, optionally with an additional topcoat of conventional polydimethylsiloxane. The syringe barrels were formed from polypropylene and coated with a conventional polydimethylsiloxane. The syringe components were subjected to irradiation, and evaluated for breakloose force and infusion pump actuation force (sticktion) relating to pump performance.

Each syringe barrel was lubricated with a conventional polydimethylsiloxane having a viscosity of 12,500 cst. Helvoet FM457 butyl rubber syringe stoppers were coated with (a) a conventional polydimethylsiloxane having a viscosity of 100,000 cst ("Control"); (b) a cured coating prepared from a coating composition consisting of a mixture of 50 weight percent of GE LSR Topcoat Part A and 50 weight percent of GE LSR Topcoat Part B according to the present invention ("Sample A"); or (c) first with a cured coating prepared from a coating composition consisting of a mixture of 50 weight percent of GE LSR Topcoat Part A and 50 weight percent of GE LSR Topcoat Part B according to the present invention and then topcoated with a conventional polydimethylsiloxane having a viscosity of 100,000 cst ("Sample B").

Each stopper was cured in an oven at a temperature of about 130-140 C. for about 10 to about 20 minutes. Each syringe was assembled and filled with 10 ml of saline solution available from VWR Products and autoclaved at 124° C. for 30 minutes.

The breakloose force (in Newtons) of each sample syringe to simulate fast speed injection was determined by an Instron Model No. 1122 in compression (injection) mode using a 50 kg compression load cell at a cross head speed of 100 mm/min. The breakloose force is visually determined as the highest peak of the curve or point of where the slope of the curve changes on the graph. The minimum sustaining force is determined as the lowest or smooth section of the curve after the breakloose force. The maximum sustaining force is determined as the highest section of the curve after the breakloose force. The values reported in Table 1 below are the average of five samples for each of Samples A and B and the Control.

Figure 1:
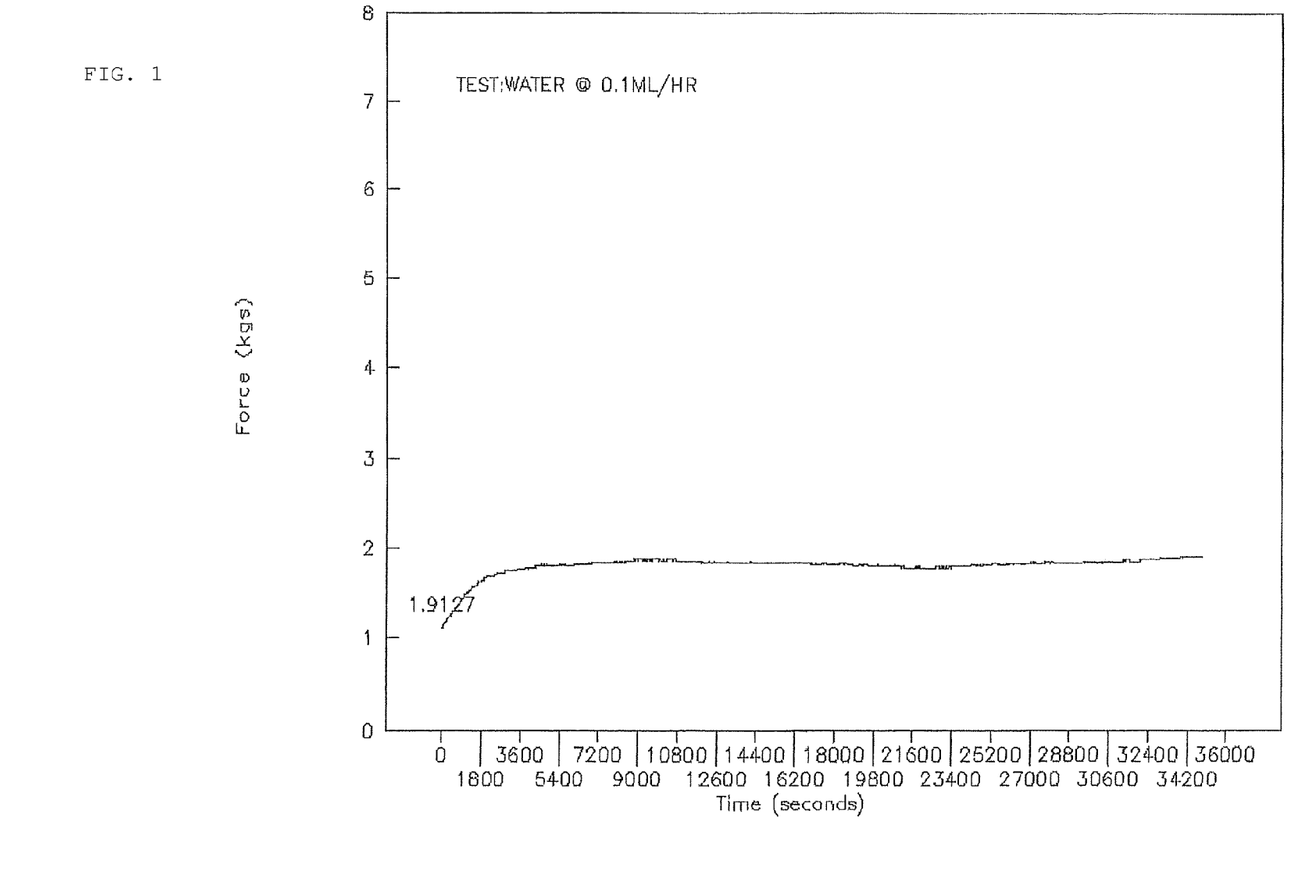
FIG. 1 is a graph of infusion pump actuation force test results at a feed rate of 0.1 ml/hr for a prior art syringe assembly.
Figure 2:
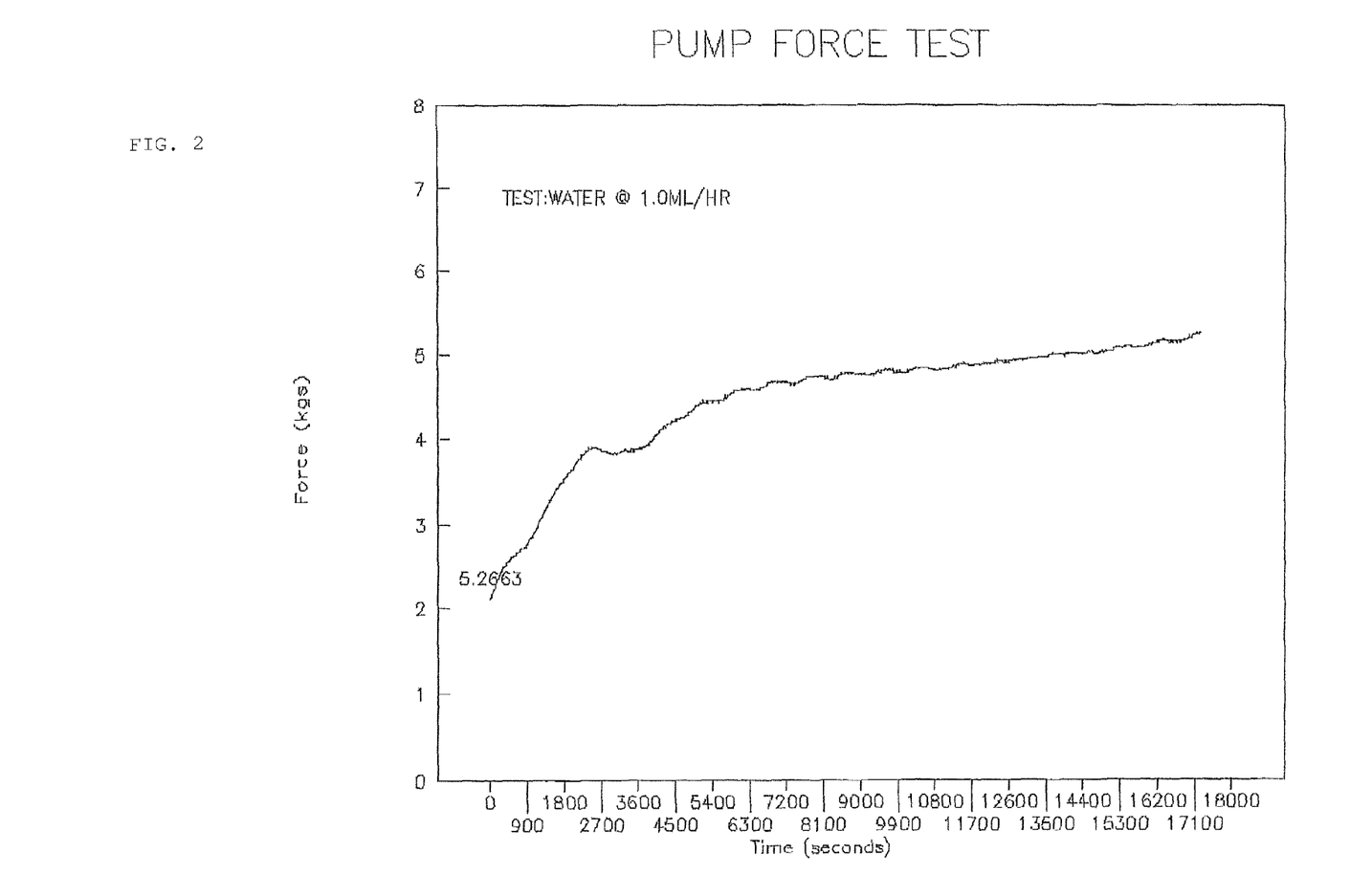
FIG. 2 is a graph of infusion pump actuation force test results at a feed rate of 1.0 ml/hr for a prior art syringe assembly.
Figure 3:
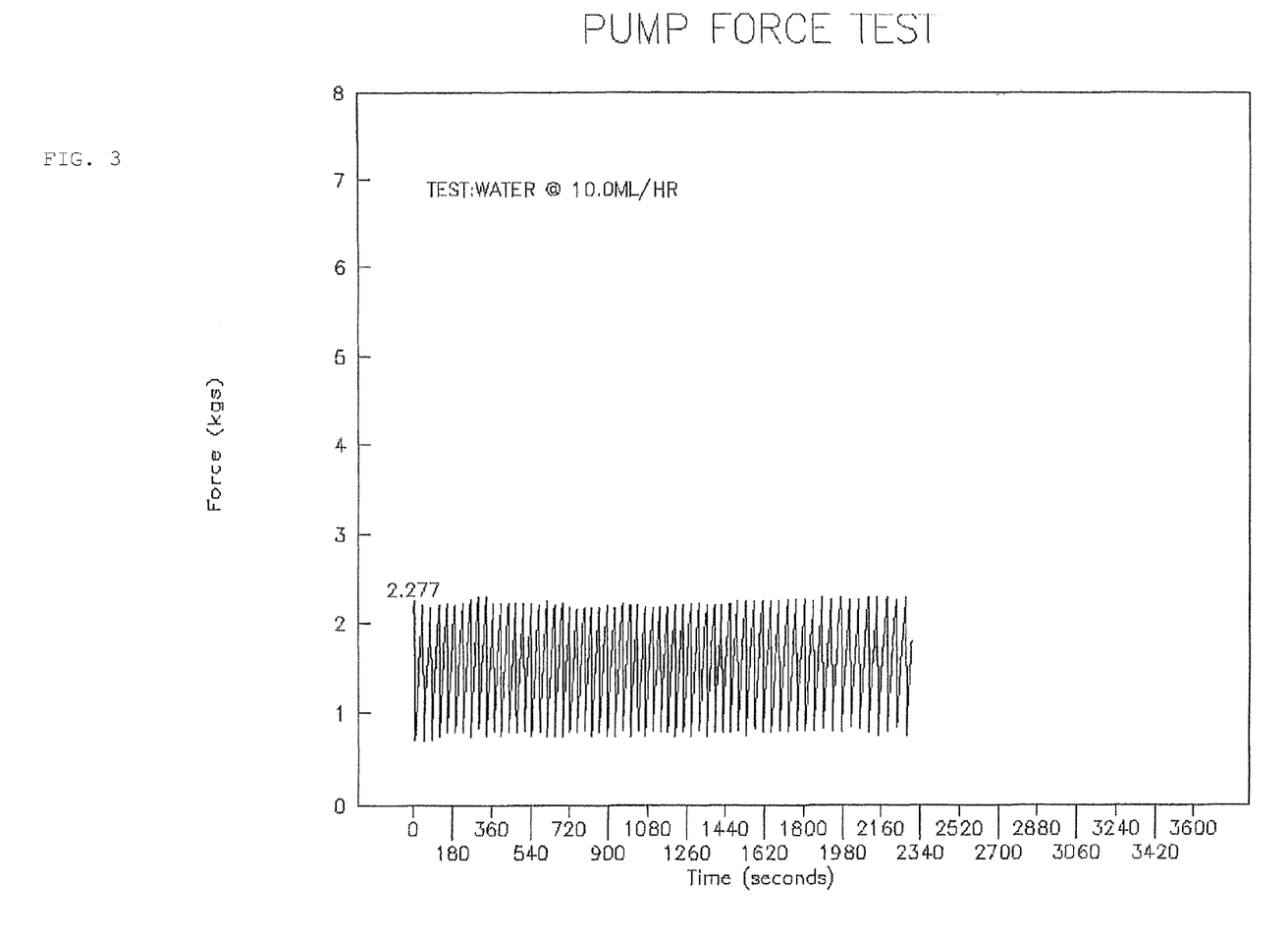
FIG. 3 is a graph of infusion pump actuation force test results at a feed rate of 10 ml/hr for a prior art syringe assembly.
Figure 4:
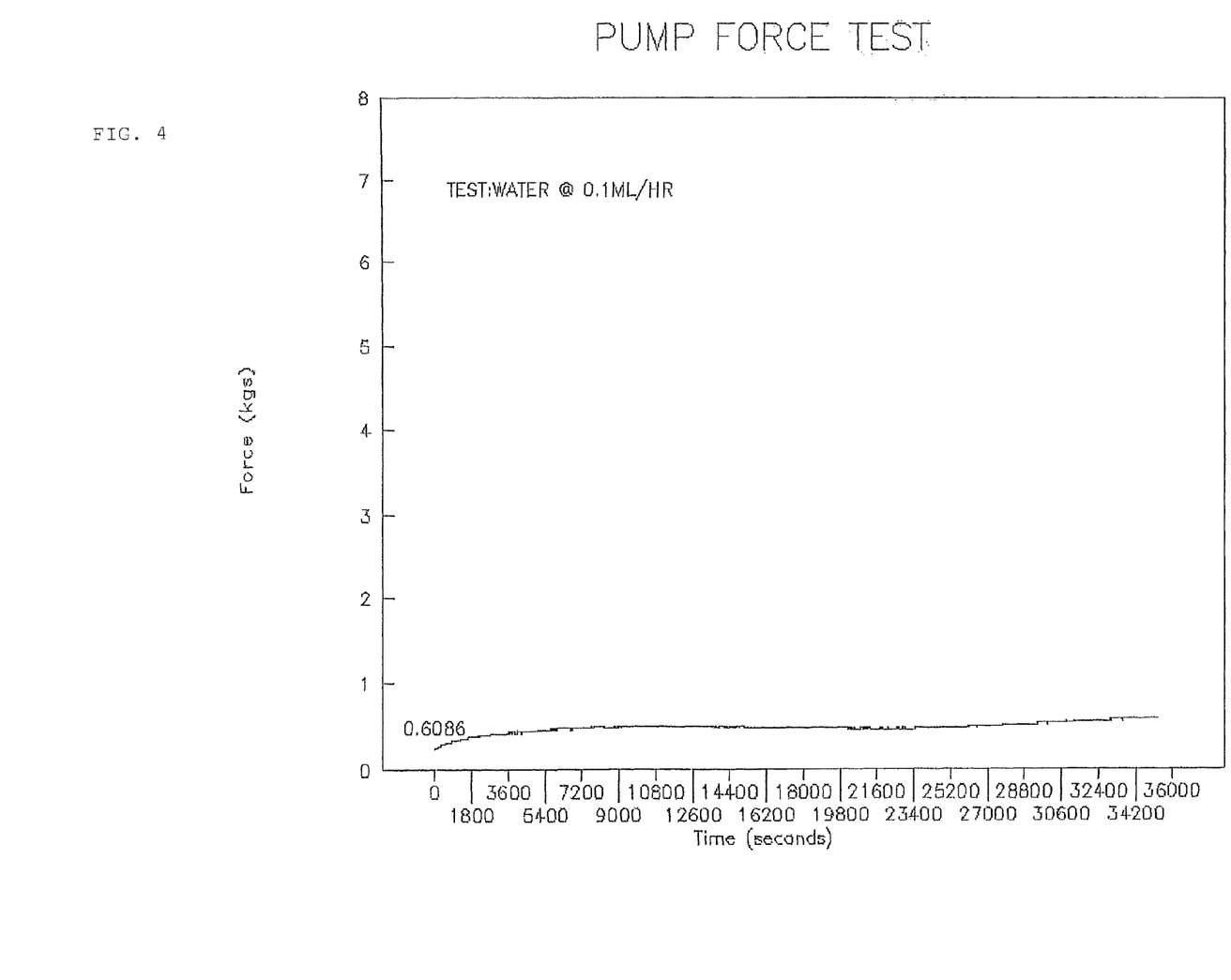
FIG. 4 is a graph of infusion pump actuation force test results at a feed rate of 0.1 ml/hr for a syringe assembly according to the present invention.
Figure 5:
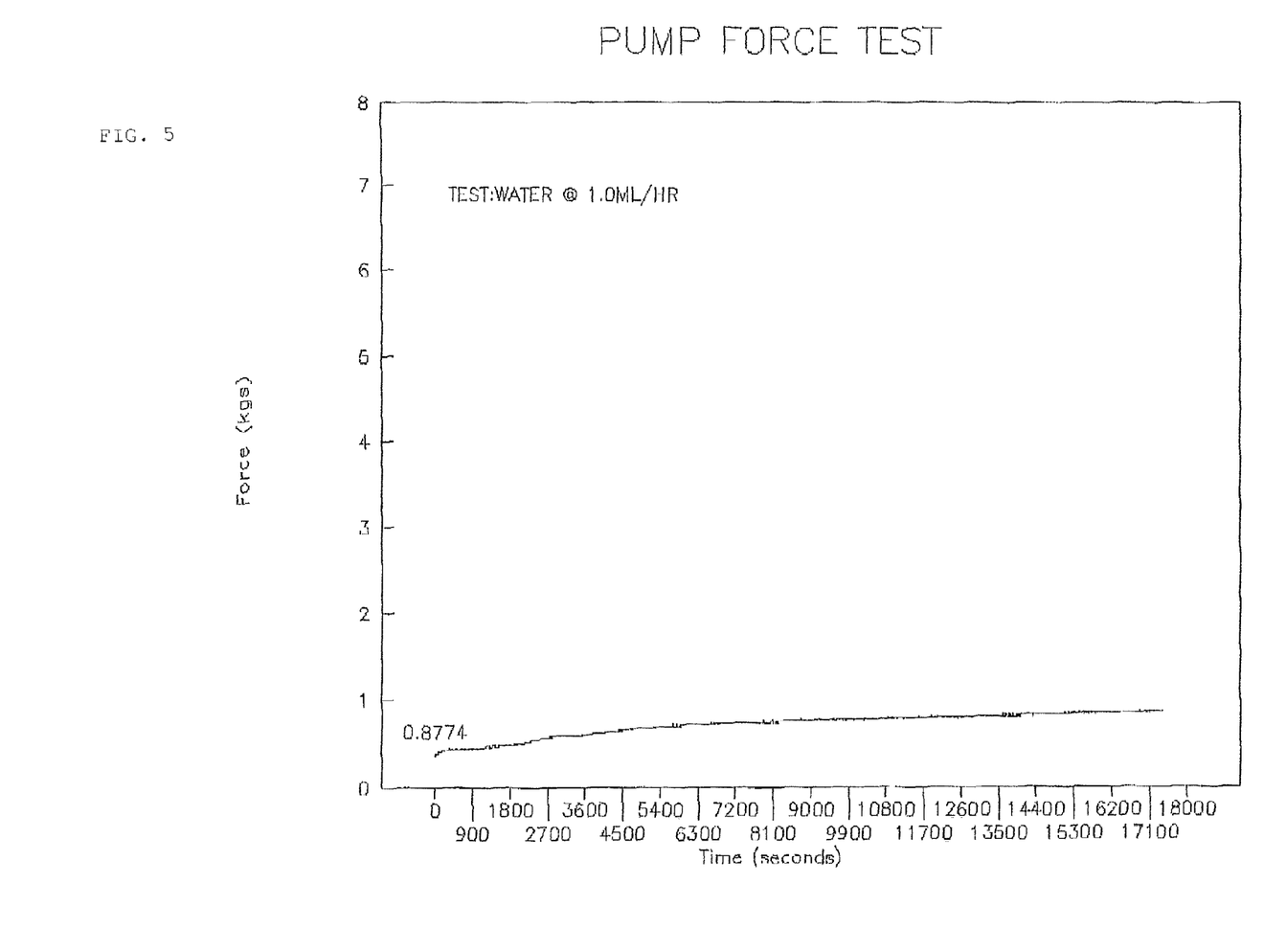
FIG. 5 is a graph of infusion pump actuation force test results at a feed rate of 1.0 ml/hr for a syringe assembly according to the present invention.
Figure 6:
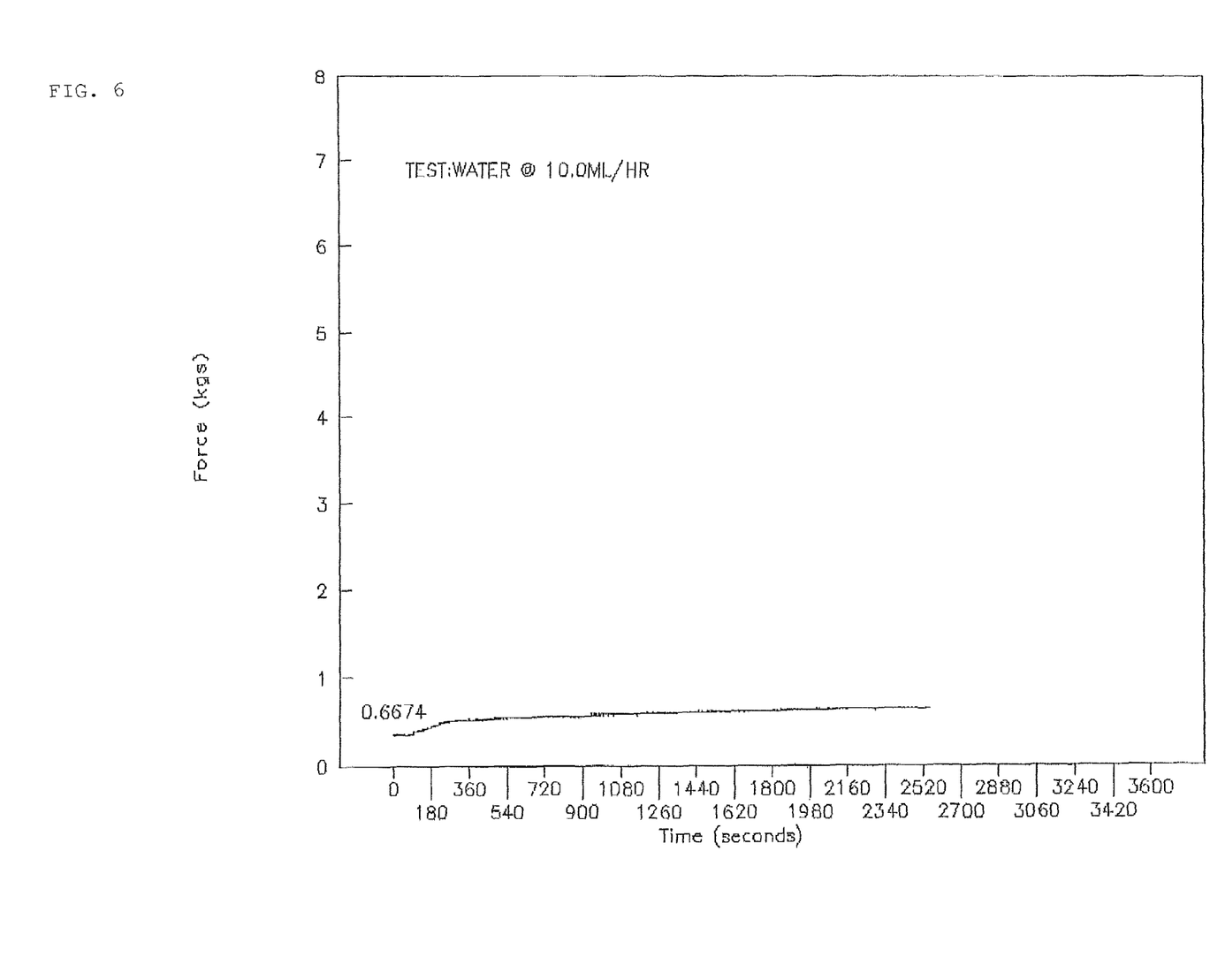
FIG. 6 is a graph of infusion pump actuation force test results at a feed rate of 10 ml/hr for a syringe assembly according to the present invention.
Figure 7:
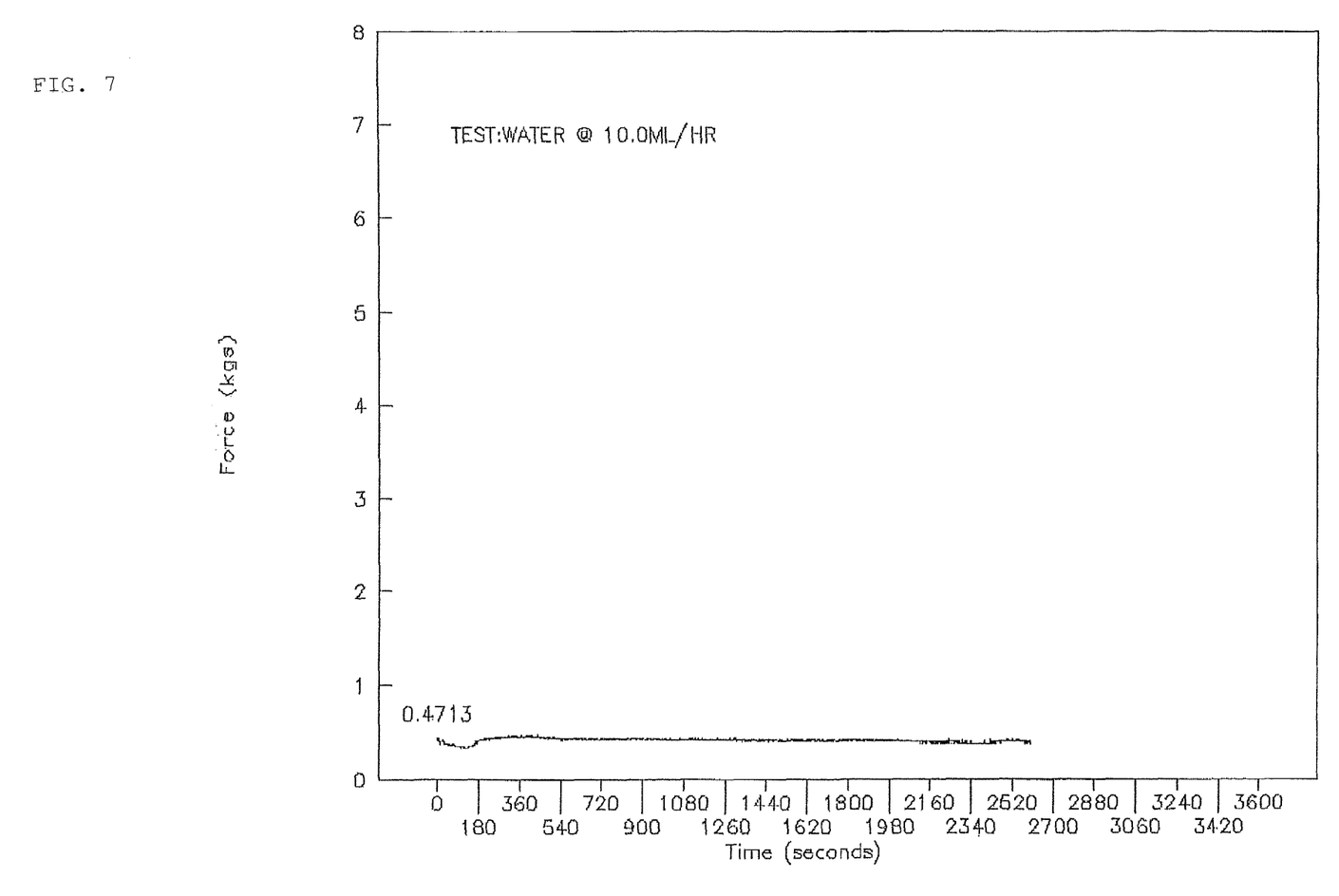
FIG. 7 is a graph of infusion pump actuation force test results at a feed rate of 10 ml/hr for a syringe assembly according to the present invention.

The infusion pump actuation force and fluid delivery characteristics for each test syringe were evaluated using an Becton Dickinson Program 2 eight pump data acquisition system. Each syringe is filled with 10 ml of Deionized water. All air bubbles in the syringe were removed and the plunger rod was advanced until the sealing rib of the stopper coincided with the desired test volume marking on the scale. Microbore tubing (0.020" ID×60" length) was connected to the syringe and the other end was connected to a 23 gauge×1 inch length needle. The needle was inserted into a beaker. The tubing set was manually filled with water from the syringe and the syringe was mounted in the pump. The flange of the barrel contected the front of the flange slot. The syringe plunger rod was positioned against the syringe pusher. There was no gap between the load cell and the plunger rod. The pump was purged by setting the flow rate at the maximum speed allowed by the pump. Once fluid is flowing freely through the tubing and needle into the beaker, the specified flow rate was set on the pump and infusion was begun. A chart of force over time for each syringe was generated, as shown in FIGS. 1-7. A visual determination of sticktion or no sticktion was made by viewing each chart for the smoothness of the curve. A smooth curve indicated no sticktion and an irregularly-shaped curve (for example with discernable peaks) indicated sticktion.

TABLE 1

|  | Sample A | Sample B | Control |
|---|---|---|---|
| Breakloose Force (N) | 22.7 ± 0.7 | 22.4 ± 1.3 | 33.2 ± 2.8 |
| Sustaining Force (N) | 10.5 ± 0.9 | 8.2 ± 0.8 | 6.7 ± 1.2 |
| Maximum Pump Actuation Force | | | |
| 0.1 ml/hr | 0.66; no sticktion | N/A | 1.77: no sticktion |
| 1.0 ml/hr | 0.91: no sticktion | N/A | 4.82: sticktion |
| 10 ml/hr | 0.49: no sticktion | 0.42: no sticktion | 1.30: sticktion |

As shown in Table 1 above and with reference to FIGS. 1-7, Sample A coated with a coating system according to the present invention exhibits lower breakloose force and reduced sticktion, compared to the Control sample coated with a conventional polydimethylsiloxane. Overcoating with a conventional polydimethylsiloxane, as in Sample B, did not appreciably lower the maximum pump actuation force.

Example 2

In this example, 10 ml syringe components were evaluated in the same manner as in Example 1 above, except the syringe barrel was formed a cyclic polyolefin. Sample C was prepared in the same manner as Sample A above. Sample D was prepared in the same manner as Sample B above. Test results are reported in Table 2 below.

TABLE 2

|  | Sample C | Sample D | Control |
|---|---|---|---|
| Breakloose Force (N) | 18.9 ± 1.7 | 19.2 ± 1.9 | 28.1 ± 10.1 |
| Sustaining Force (N) | 10.1 ± 0.7 | 10.8 ± 0.8 | 7.8 ± 0.2 |

As shown in Table 2 above, Sample C coated with a coating system according to the present invention exhibits lower breakloose force compared to the Control sample coated with a conventional polydimethylsiloxane. Overcoating with a conventional polydimethylsiloxane, as in Sample B, did not appreciably affect the breakloose or sustaining forces.

The present invention has been described with reference to specific details of particular embodiments thereof. It is not intended that such details be regarded as limitations upon the scope of the invention except insofar as and to the extent that they are included in the accompanying claims.

What is claimed is:

1. A rubber sealing member for a medical device, the rubber sealing member being formed from polyisoprene rubber, butyl rubber or elastomeric styrene copolymer and having an exterior surface adapted to sealingly engage an inner surface of a chamber of the medical device, the exterior surface of the sealing member having a coating thereon prepared from a curable composition comprising:
    (a) a first organopolysiloxane comprising at least two alkenyl groups;
    (b) a second organopolysiloxane comprising at least two pendant hydrogen groups, the second organopolysiloxane being different from the first organopolysiloxane; and
    (c) a cyclic organosiloxane.

2. The rubber sealing member according to claim 1, wherein the rubber sealing member is selected from the group consisting of a stopper, O-ring, plunger tip and piston.

3. The rubber sealing member according to claim 1, wherein the rubber sealing member is formed from butyl rubber or elastomeric styrene copolymer.

4. The rubber sealing member according to claim 1, wherein each alkenyl group of the first organopolysiloxane (a) is independently selected from the group consisting of vinyl, allyl, propenyl, butenyl, pentenyl, hexenyl, heptenyl, octenyl, nonenyl and decenyl.

5. The rubber sealing member according to claim 1, wherein at least one alkenyl group of organopolysiloxane (a) is vinyl.

6. The rubber sealing member according to claim 5, wherein the first organopolysiloxane (a) is (7.0-8.0% vinylmethylsiloxane)-dimethylsiloxane copolymer, trimethylsiloxy terminated.

7. The rubber sealing member according to claim 1, wherein the first organopolysiloxane (a) further comprises at least one fluoro group.

8. The rubber sealing member according to claim 1, wherein the first organopolysiloxane (a) comprises about 5 to about 50 weight percent of the composition.

9. The rubber sealing member according to claim 1, wherein the second organopolysiloxane (b) is represented by the structural formula (V):

(V)

wherein p is about 8 to about 12, for example about 10.

10. The rubber sealing member according to claim 1, wherein the second organopolysiloxane (b) is represented by the structural formula (VI):

$$HMe_2SiO(Me_2SiO)_pSiMe_2H \qquad (VI)$$

wherein p is about 140 to about 170.

11. The rubber sealing member according to claim 1, wherein the second organopolysiloxane (b) is selected from the group consisting of dimethylhydro terminated polydimethylsiloxanes; methylhydro, dimethylpolysiloxanecopolymers; methylhydro methyloctyl siloxane copolymers; and methylhydro, phenylmethyl siloxane copolymers.

12. The rubber sealing member according to claim 1, wherein the second organopolysiloxane (b) further comprises at least one fluoro group.

13. The rubber sealing member according to claim 1, wherein the second organopolysiloxane (b) comprises about 1 to about 40 weight percent of the composition.

14. The rubber sealing member according to claim 1, wherein the composition further comprises a third component selected from the group consisting of fluorocarbon oligomers, fluorocarbon polymers and fluoro organopolysiloxanes.

15. The rubber sealing member according to claim 14, wherein the third component comprises at least one fluoro group selected from the group consisting of fluorine groups and fluoroalkyl groups.

16. The rubber sealing member according to claim 1, wherein the at least one cyclic siloxane is selected from the group consisting of octamethylcyclotetrasiloxane and decamethylcyclopentasiloxane.

17. The rubber sealing member according to claim 1, wherein the cyclic siloxane comprises about 5 to about 80 weight percent of the composition.

18. The rubber sealing member according to claim 1, wherein the composition further comprises polydimethylsiloxane.

19. The rubber sealing member according to claim 18, wherein the polydimethylsiloxane comprises about 1 to about 20 weight percent of the composition.

20. The rubber sealing member according to claim 1, wherein the composition further comprises silica.

21. The rubber sealing member according to claim 20, wherein the silica comprises about 1 to about 15 weight percent of the composition.

22. The rubber sealing member according to claim 1, wherein the composition further comprises a catalytic amount of a catalyst for promoting crosslinking of the first organopolysiloxane (a) and the second organopolysiloxane (b).

23. The rubber sealing member according to claim 22, wherein the catalyst is selected from the group consisting of platinum, rhodium and peroxides.

24. The rubber sealing member according to claim 22, wherein the catalyst comprises about 0.001 to about 0.05 weight percent of the composition.

25. A medical device comprising:
(a) a chamber comprising an inner surface for containing a medicament; and
(b) a rubber sealing member according to claim 1.

26. The medical device according to claim 25, wherein the medical device is selected from the group consisting of syringe assemblies, syringe pumps, drug cartridges, needleless injectors, liquid dispensing devices and liquid metering devices.

27. The medical device according to claim 25, wherein the chamber is formed from glass, metal, ceramic, plastic, rubber or combinations thereof.

28. The medical device according to claim 27, wherein the chamber is prepared from an olefinic polymer.

29. The medical device according to claim 28, wherein the olefinic polymer is selected from the group consisting of polyethylene, polypropylene, poly (1-butene), poly(2-methyl-1-pentene) and cyclic polyolefins.

30. The medical device according to claim 29, wherein the chamber is prepared from a cyclic polyolefin.

31. The rubber sealing member according to claim 1, wherein at least one of the first organopolysiloxane, the second organopolysiloxane or an optional third component of the curable composition comprises at least one fluoro group.

32. A method for lubricating the interface between an inner surface of a chamber and an exterior surface of a rubber sealing member of a medical device, comprising the steps of:
(a) applying a coating onto the exterior surface of the rubber sealing member, the rubber sealing member being formed from polyisoprene rubber, butyl rubber or elastomeric styrene copolymer, the coating being prepared from a curable composition comprising:
(i) a first organopolysiloxane comprising at least two alkenyl groups;
(ii) a second organopolysiloxane comprising at least two pendant hydrogen groups, the second organopolysiloxane being different from the first organopolysiloxane; and
(iii) a cyclic organosiloxane; and
(b) at least partially crosslinking the coating of step (a).

33. The method according to claim 32, wherein at least one of the first organopolysiloxane, the second organopolysiloxane or an optional third component of the curable composition comprises at least one fluoro group.

34. A method for reducing breakout force or breakloose force between an inner surface of a chamber and an exterior surface of a rubber sealing member of a medical device, comprising the steps of:
(a) applying a coating onto the exterior surface of the rubber sealing member, the rubber sealing member being formed from polyisoprene rubber, butyl rubber or elastomeric styrene copolymer, the coating being prepared from a curable composition comprising:
(i) a first organopolysiloxane comprising at least two alkenyl groups;
(ii) a second organopolysiloxane comprising at least two pendant hydrogen groups, the second organopolysiloxane being different from the first organopolysiloxane; and
(iii) a cyclic organosiloxane; and
(b) at least partially crosslinking the coating of step (a).

35. The method according to claim 34, wherein at least one of the first organopolysiloxane, the second organopolysiloxane or an optional third component of the curable composition comprises at least one fluoro group.

36. A method for reducing sustaining force between an inner surface of a chamber and an exterior surface of a rubber sealing member of a medical device, comprising the steps of:
(a) applying a coating onto the exterior surface of the rubber sealing member, the rubber sealing member being formed from polyisoprene rubber, butyl rubber or elastomeric styrene copolymer, the coating being prepared from a curable composition comprising:
(i) a first organopolysiloxane comprising at least two alkenyl groups;
(ii) a second organopolysiloxane comprising at least two pendant hydrogen groups, the second organopolysiloxane being different from the first organopolysiloxane; and
(iii) a cyclic organosiloxane; and
(b) at least partially crosslinking the coating of step (a).

37. The method according to claim 36, wherein at least one of the first organopolysiloxane, the second organopolysiloxane or an optional third component of the curable composition comprises at least one fluoro group.

38. A method for reducing breakloose and sustaining forces between an inner surface of a chamber and an exterior surface of a rubber sealing member of a medical device, comprising the steps of:
(a) applying a coating onto the exterior surface of the rubber sealing member, the rubber sealing member being formed from polyisoprene rubber, butyl rubber or elastomeric styrene copolymer, the coating being prepared from a curable composition comprising:
(i) a first organopolysiloxane comprising at least two alkenyl groups;
(ii) a second organopolysiloxane comprising at least two pendant hydrogen groups, the second organopolysiloxane being different from the first organopolysiloxane; and
(iii) a cyclic organosiloxane; and
(b) at least partially crosslinking the coating of step (a).

39. The method according to claim 38, wherein at least one of the first organopolysiloxane, the second organopolysiloxane or an optional third component of the curable composition comprises at least one fluoro group.

* * * * *